United States Patent [19]

Petit

[11] Patent Number: 4,760,837

[45] Date of Patent: Aug. 2, 1988

[54] APPARATUS FOR VERIFYING THE POSITION OF NEEDLE TIP WITHIN THE INJECTION RESERVOIR OF AN IMPLANTABLE MEDICAL DEVICE

[75] Inventor: Michael G. Petit, Santa Barbara, Calif.

[73] Assignee: Inamed Development Company, Santa Barbara, Calif.

[21] Appl. No.: 16,251

[22] Filed: Feb. 19, 1987

[51] Int. Cl.$^4$ ............................................... A61B 19/00
[52] U.S. Cl. ....................................... 128/1 R; 604/9; 604/93; 604/175; 116/DIG. 17
[58] Field of Search ...................... 128/1 R; 604/8–10, 604/93, 131, 175, 891, 185; 116/D 17, 205

[56] References Cited

U.S. PATENT DOCUMENTS 4,557,722  12/1985  Harris ........................................ 604/9

Primary Examiner—Dalton L. Truluck
Assistant Examiner—Denise Whelton
Attorney, Agent, or Firm—Michael G. Petit

[57] ABSTRACT

An improved injection reservoir for medically implantable devices is disclosed, the improvement means for (a) verifying that the tip of the needle is actually in the injection reservoir prior to injection; and (b) reducing damage to the needle tip during the verification procedure. In the preferred embodiment flexible needle guard provides first contact with a needle entering the reservoir. Further pressure on the needle results in movement of the needle guard causing brushes attached thereto to slide against a roughened surface housed within the reservoir causing a mechanical vibration which can be either felt with the fingers via transmission up the needle or heard with a stethoscope placed on the skin in the vicinity of the reservoir. The surface of the flexible needle is coated with a layer of hard biocompatible elastomer to further reduce damage to the needle tip during position verification.

9 Claims, 1 Drawing Sheet

PRIOR ART

APPARATUS FOR VERIFYING THE POSITION OF NEEDLE TIP WITHIN THE INJECTION RESERVOIR OF AN IMPLANTABLE MEDICAL DEVICE

BACKGROUND OF INVENTION

Implantable medical devices containing a reservoir which requires filling, periodic refilling or sampling are well known in medicine. Such devices or fill ports usually contain a needle penetrable, fluid impermeable septum forming at least a portion of the housing through which access to the interior of the housing, which defines a reservoir, may be gained by insertion of a hypodermic needle. In practice, the location of the fill port under the skin is first determined by extracorporeal means such as digital palpation or magnetic detection, then the hypodermic needle is driven through the skin in such a way as to puncture the septum. After the needle penetrates the septum it passes on through the reservoir until the tip comes to rest against a needle guard which provides a barrier to further progress of the needle. When the physician encounters the resistance of the needle guard and is confident that the needle tip is in the reservoir, the reservoir is filled by means of a syringe. When filling is complete, the needle is withdrawn.

While puncture of the septum usually causes minimal damage to the needle tip, contact with the needle guard can cause burring. The burring can be particularly severe if the physician taps the needle against the guard to verify correct positioning of the needle within the reservoir. Such a burred needle when withdrawn through the septum may cut or tear the elastomeric material thus reducing its tendency to self seal.

It is the object of the invention to provide an improved fill port for injection of fluids into an implanted reservoir, the improvement being positive and objective means for ascertaining correct positioning of the needle tip within the reservoir by induction of a characteristic externally mechanical vibration detectable in response to the mechanical exertion of pressure by the needle upon a flexible member situated within the reservoir. It is a further object of this invention to prevent or minimize burring of a needle used to fill an implantable injection reservoir.

BRIEF DESCRIPTION OF THE DRAWINGS

The invention will become better understood by reference to the accompanying drawings wherein.

DESCRIPTION OF THE PREFERRED EMBODIMENT

Figure 1:
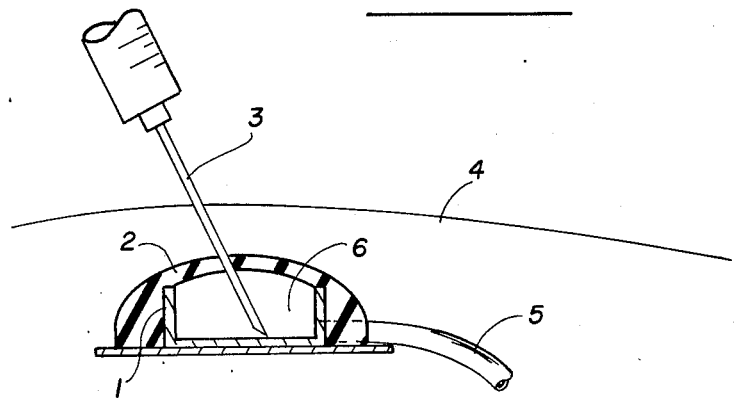
FIG. 1 is a cutaway schematic of a conventional implantable prior art fill port. Needle (3) punctures skin (4) and passes through septum (2) until it encounters resistance to further progress by contacting barrier (1) (the needle guard). When continued downward pressure on needle (3) results in no further progress of needle (3), it is generally assumed that the needle tip is correctly positioned in the reservoir (6). A fluid is then injected into the reservoir which may then pass to a remote site through conduit (5) affixed to and in fluid communication with with the injection reservoir.
Figure 2:
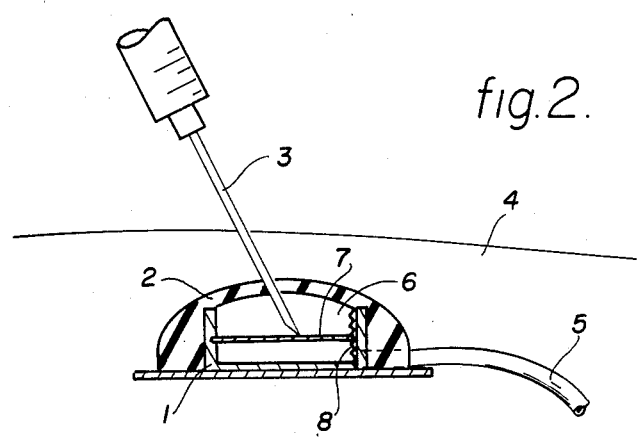
FIG. 2 is a cutaway schematic of a conventional prior art implantable fill port containing two new elements: a flexible member (7) and a roughened surface (8). When the needle (3) encounters flexible member (7) further pressure results in flexion of (7). The tip of flexible member (7) rubs against rough surface (8) providing a grating sound and a "scratchy feel" which can be detected either by the finger tips or by means of a stethoscope placed on the skin (4) proximal to the device When pressure on flexible member (7) is released, for example, by backing off on the needle (3), the flexible member (7) returns to its rest position.
Figure 3:
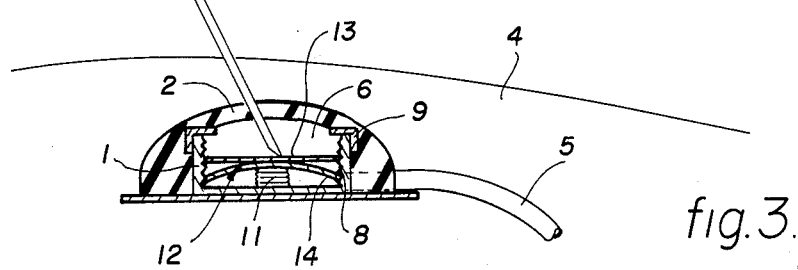
FIG. 3 is a schematic view of a preferred embodiment in which the flexible first member takes the form of a spring loaded (11) needle receiving plate (13) with brushes (14) affixed so as to press against the roughened surface of second member (1) which, in this embodiment, also serves as a needle guard.
Figure 4:
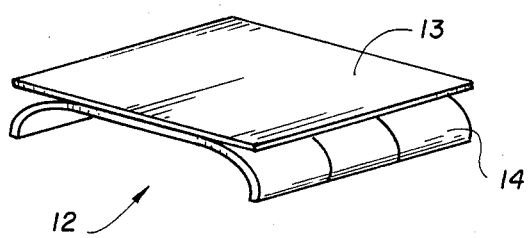

In FIG. 3, needle (3) punctures skin (4) and passes through underlying tissue to puncture septum (2) where it contacts a first barrier (12) supported within the reservoir by a flexible member (11). First barrier (12) consists of a flat needle receiving plate (13) and brushes (14) affixed to the bottom thereof disposed to press against roughened surface (8). Continued pressure on needle 3 causes flexion of support material (11) and movement of barrier brushes (14) against the roughened surface of the needle guard (1) which causes a characteristic vibration which may be detected by a stethoscope placed on the skin near the needle or by the fingertips as the mechanical vibration is transmitted up the needle to the shank. When pressure on first barrier (12) by needle (3) is released, compressed support member (11) forces first barrier (12) up until it comes to rest against detents (9). In the preferred embodiment first barrier (12) is 316L stainless steel of 0.010" thickness. Flexible support material (11) is a length of 5 mm o.d. porous silicone tubing. The first barrier (12) is coated with silicone rubber and/or teflon to cushion the impact of needle (3) with the surface of first barrier (12) and thereby prevent burring. the brushes (14) shown in the FIG. 3 inset are thin strips of 0.002" thick 316L stainless steel.

What I claim is:

1. An improved bi-directional fill port for use in conjunction with a hypodermic needle for emptying and filling a subcutaneous fluid reservoir comprising a housing defining a reservoir wherein at least a portion of said housing further comprises a fluid impermeable needle-penetrable septum, the improvement comprising (A) a flexible first member disposed within said reservoir substantially underlying said septum such that when said needle pierces said septum and enters said reservoir said needle will push against said first member causing it to move; and (B) A second member disposed in juxtaposition to said first member, said first and second members providing noise making means such that movement of said first member against said second member produces an extracorporeally detectable mechanical vibration with at least one frequency component being within the range of 0–20 KHZ.

2. The apparatus defined in claim 1 wherein said first member comprises a substantially rigid biocompatible material supported by a flexible member.

3. The apparatus of claim 2 wherein said biocompatible material is 316L stainless steel.

4. The apparatus of claim 2 wherein said flexible member is a stainless steel spring.

5. The apparatus of claim 2 wherein said substantially rigid biocompatible material is coated with a second biocompatible material to prevent or minimize damage to the tip of said hypodermic needle.

6. The apparatus of claim 5 wherein said second biocompatible material is silicone rubber.

7. The apparatus of claim 1 wherein said second member is a biocompatible material.

8. The apparatus of claim 7 wherein said biocompatible material is stainless steel.

9. The apparatus of claim 7 wherein at least a portion of the surface of the stainless steel is roughened.

* * * * *